(12) United States Patent
Closson et al.

(10) Patent No.: US 7,820,616 B1
(45) Date of Patent: Oct. 26, 2010

(54) CYCLIC ACETAL COMPOUNDS AND THEIR USE IN PERFUME COMPOSITIONS

(75) Inventors: Adam P. Closson, Red Bank, NJ (US); Michael G. Monteleone, Hazlet, NJ (US)

(73) Assignee: International Flavors & Fragrances, Inc., New York, NY (US)

( * ) Notice: Subject to any disclaimer, the term of this patent is extended or adjusted under 35 U.S.C. 154(b) by 0 days.

(21) Appl. No.: 12/481,155

(22) Filed: Jun. 9, 2009

(51) Int. Cl.
*A61K 8/49* (2006.01)
*C07D 493/08* (2006.01)
(52) U.S. Cl. .................. 512/12; 510/103; 549/397
(58) Field of Classification Search ............. 549/397; 512/12; 510/103
See application file for complete search history.

(56) References Cited

U.S. PATENT DOCUMENTS

| 4,108,870 A | 8/1978 | Fried et al. |
| 4,839,383 A | 6/1989 | Vite |

FOREIGN PATENT DOCUMENTS

| DE | 3619136 C2 | 3/1989 |
| NL | 69308 | 1/1952 |

OTHER PUBLICATIONS

C.S. Marvel et al. "The preparation of 2-alkylbutadienes" J. Am. Chem. Soc. (1948) 70, 1694-1699.

R. Ter Heide et al. "Flavor constituents in rum" Qual. Foods Beverages: Chemical Technol. 2nd (1981), 1, 183-200.

Miguel Yus et al. "One-step synthesis of substituted 6,8-dioxabicyclo [3.2.1]octanes: easy preparation of racemic frontalin, brevicomins, and related systems" Journal of Organic Chemistry (1992), 57(2), 750-751.

Kenshu Fujiwara et al. "Novel oxepane formation by TiCl4-catalyzed nucleophilic cleavage of 1-alkoxymethyl-6,8-dioxabicyclo[3.2.1]octanes" Tetrahedron (2000), 56(8), 1065-1080.

Andreas Steinreiber et al. "Asymmetric total synthesis of a beer-aroma constituent based on enantioconvergent biocatalytic hydrolysis of trisubstituted epoxides" Synthesis (2001), 13, 2035-2039.

*Primary Examiner*—Bernard Dentz
(74) *Attorney, Agent, or Firm*—Elizabeth M. Quirk; XuFan Tseng; Joseph F. Leightner

(57) ABSTRACT

The present invention a method of improving, enhancing, or modifying a fragrance formulation through the addition of an olfactory acceptable amount of the following compound:

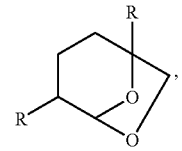

wherein R represents a saturated $C_2$-$C_4$ alkyl straight chain or branched.

17 Claims, No Drawings

CYCLIC ACETAL COMPOUNDS AND THEIR USE IN PERFUME COMPOSITIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes, and personal care products. Those with skill in the art appreciate how small variations in the chemical structures can result in significant differences in the odor, notes, and characteristics of the molecules. The discoveries and development of new fragrance compounds with these variations allow the perfumers to apply new chemicals in creating new fragrances.

SUMMARY OF THE INVENTION

The present invention provides novel chemicals, and the use of the chemicals to enhance the fragrance of perfumes, toilet waters, colognes, personal products and the like.

More specifically, the present invention is directed to cyclic acetal compounds and a method of improving, enhancing, or modifying a fragrance formulation through the addition of an olfactory acceptable amount of cyclic acetal compounds represented by Formula I set forth below:

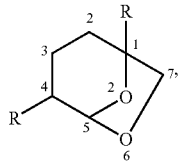

Formula I wherein R represents a saturated $C_2$-$C_4$ alkyl straight chain or branched.

The present invention is directed to the surprising finding of a fruity note of the cyclic acetal compounds provided above as well as their unexpected advantageous use in perfumery.

Another embodiment of the invention is directed to a fragrance formulation comprising the cyclic acetal compounds provided above.

Another embodiment of the invention is directed to a method of improving, enhancing, or modifying a fragrance formulation by incorporating an olfactory acceptable amount of the cyclic acetal compounds provided above.

These and other embodiments of the present invention will be apparent by reading the following specification.

DETAILED DESCRIPTION OF THE INVENTION

It has been surprisingly discovered that the cyclic acetal compounds provided above, which contain two identical saturated alkyl substituents at 1 and 4 positions of the bicycle octane ring and each substituent consists of a specific chain length of 2-4 carbons, possess an unexpected fruity note and therefore have unexpected advantageous use in perfumery.

It is known to those with the skill in the art that Formula I as defined above provides the following novel compounds:

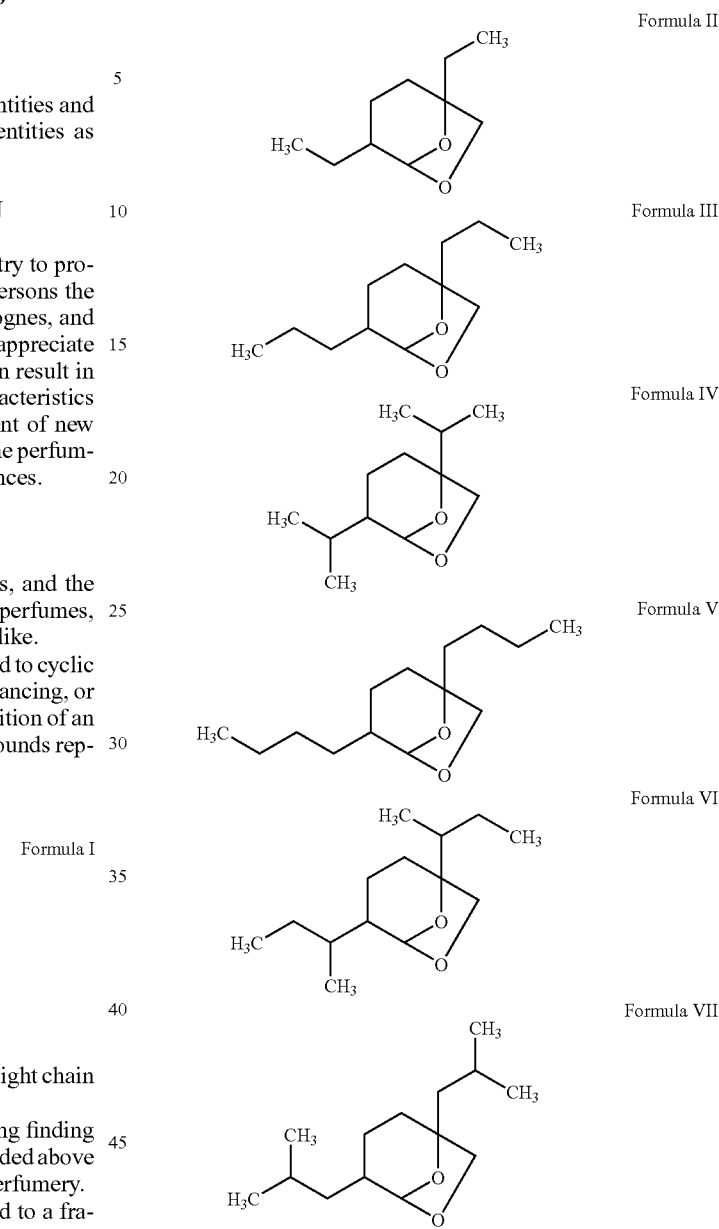

Those with the skill in the art will recognize that:

Formula II represents 1,4-diethyl-6,8-dioxa-bicyclo[3.2.1]octane;

Formula III represents 1,4-dipropyl-6,8-dioxa-bicyclo [3.2.1]octane;

Formula IV represents 1,4-diisopropyl-6,8-dioxa-bicyclo [3.2.1]octane;

Formula V represents 1,4-dibutyl-6,8-dioxa-bicyclo [3.2.1]octane;

Formula VI represents 1,4-di-sec-butyl-6,8-dioxa-bicyclo [3.2.1]octane; and

Formula VII represents 1,4-diisobutyl-6,8-dioxa-bicyclo [3.2.1]octane.

It has been unexpectedly discovered that 1,4-diethyl-6,8-dioxa-bicyclo[3.2.1]octane (Formula II) possesses fruity, spicy, herbal, tea-note, anisic, and estragol notes; 1,4-dipropyl-6,8-dioxa-bicyclo[3.2.1]octane (Formula III) possesses latex, fruity, and sour notes; 1,4-diisopropyl-6,8-dioxa-bicyclo[3.2.1]octane (Formula IV) possesses fruity, lactonic, green, woody, floral, and waxy notes; and 1,4-dibutyl-6,8-dioxa-bicyclo[3.2.1]octane (Formula V) fruity, green, and woody notes.

The compounds of the present invention may be prepared via thermal dimerization of α-methylene aldehydes, followed by reduction and cyclization. The reaction steps can be depicted by a general scheme as follows:

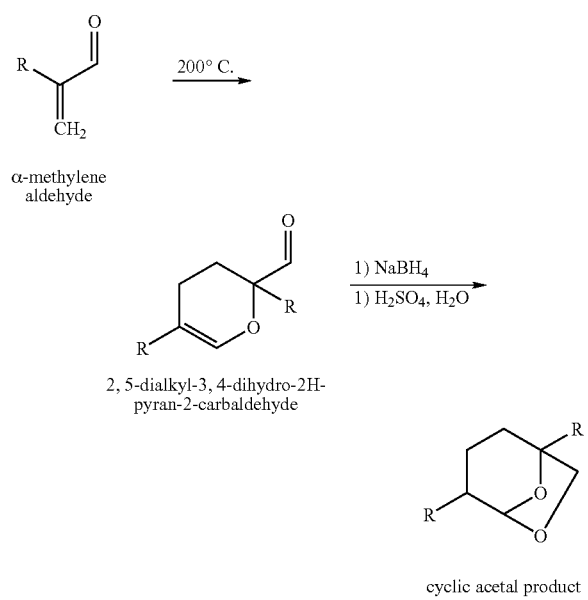

wherein R is defined as above;
NaBH$_4$ represents sodium borohydride; and
H$_2$SO$_4$ represents sulfuric acid.

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

The use of the compounds of the present invention is widely applicable in current perfumery products, including the preparation of perfumes and colognes, the perfuming of personal care products such as soaps, shower gels, and hair care products, fabric care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory acceptable amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of the claimed compounds employed in a perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, mL is understood to be milliliter, g is understood to be gram, and mol is understood to be mole. IFF as used in the examples is understood to mean International Flavors & Fragrances Inc., New York, N.Y., USA.

Example I

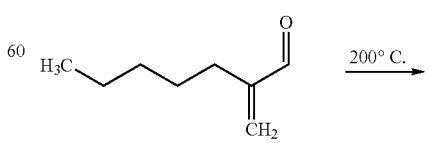

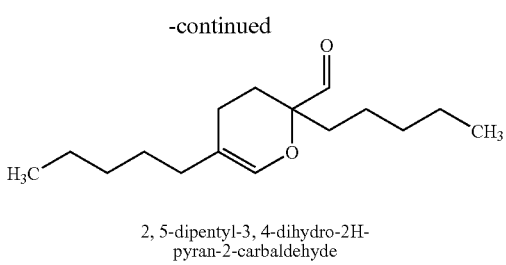

2, 5-dipentyl-3, 4-dihydro-2H-pyran-2-carbaldehyde

Preparation of
2,5-Dipentyl-3,4-dihydro-2H-pyran-2-carbaldehyde

2-Methylene-heptanal was prepared with heptanal, formaldehyde, di-n-butylamine, and acetic acid (all commercially available from Sigma-Aldrich Inc.) via the known Mannich reaction followed by an elimination reaction (Marvel, C. S., et al. J. Am. Chem. Soc. 1948, 70:1694-1699). Crude 2-methylene-heptanal (582 g) was loaded into a 2-liter stainless steel pressure reactor. The reactor was sealed and heated to 200° C. The reaction mixture was periodically sampled and analyzed by Gas Chromatography ("GC") to monitor the reaction progress. After a conversion rate of about 90% was reached, the reaction was cooled. The crude product was purified by distillation to provide 2,5-dipentyl-3,4-dihydro-2H-pyran-2-carbaldehyde (360 g).

$^1$H NMR (CDCl$_3$, 500 MHz): 0.87 ppm (t, 6H, J=7.13 Hz), 1.16-1.36 ppm (m, 11H), 1.39-1.46 ppm (m, 1H), 1.53-1.60 ppm (m, 1H), 1.61-1.71 ppm (m, 2H), 1.80-1.86 ppm (m, 4H), 2.05-2.11 ppm (m, 1H), 6.36 ppm (s, 1H), 9.56 ppm (s, 1H).

Example II

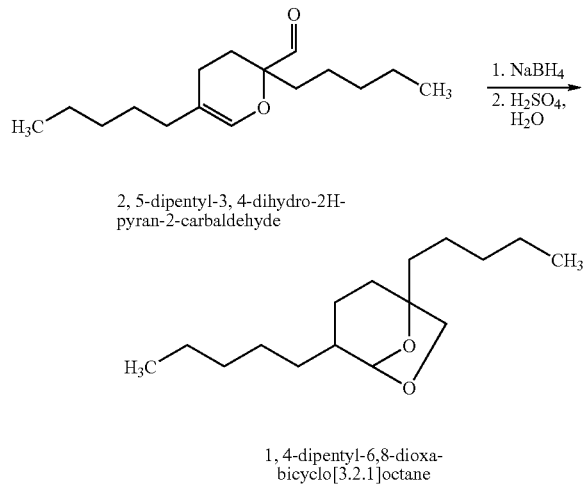

Preparation of
1,4-Dipentyl-6,8-dioxa-bicyclo[3.2.1]octane 2,5-dipentyl-3,4-dihydro-2H-pyran-2-carbaldehyde (165 g, synthesized as above) was loaded in a 3-liter round bottom flask and dissolved in 500 mL of isopropanol. Sodium Borohydride (6.1 g, commercially available from Sigma-Aldrich Inc) was added and the reaction exothermed up to about 58° C. The reaction was then stirred for about 2 hours. The reaction mixture was periodically sampled and analyzed by GC to monitor the reaction progress. After GC indicated the consumption of about all the starting material, sulfuric acid (500 mL, 10% solution in water) was then added and the temperature was increased to 35° C. The reaction mixture was further stirred for about 30 minutes and then cooled. The organic layer was separated and washed with 500 mL 10% aqueous sodium hydroxide solution. The solvents were removed to yield the crude product, which was purified by distillation to provide 1,4-dipentyl-6,8-dioxa-bicyclo[3.2.1]octane (128 g).

$^1$H NMR (CDCl$_3$, 500 MHz): 0.85-0.91 ppm (m, 6H), 1.22-1.36 ppm (s, 12H), 1.36-1.77 ppm (m, ~8.33H), 1.90-2.00 ppm (m, ~0.67H), 3.38-3.42 ppm (m, 1H), 3.80 ppm (dd, ~0.33H, J=6.74, 2.49 Hz), 3.87 ppm (dd, ~0.67H, J=6.81, 2.44 Hz), 5.27 ppm (s, ~0.33H), 5.31 ppm (s, ~0.67H).

Example III

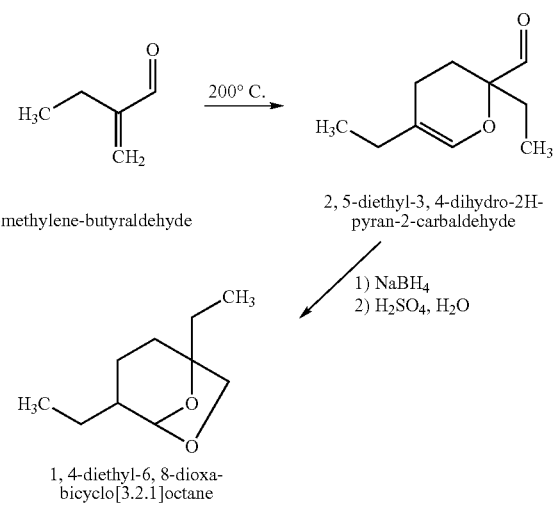

Preparation of
1,4-Diethyl-6,8-dioxa-bicyclo[3.2.1]octane (Formula II)

2-Methylene butanal (314 g, prepared the same as above via the Mannich reaction followed by the elimination reaction) was first applied to the Example I scheme described above to produce 2,5-diethyl-3,4-dihydro-2H-pyran-2-carbaldehyde (154 g), which was subsequently applied to the Example II scheme described above to provide 1,4-diethyl-6,8-dioxa-bicyclo[3.2.1]octane (111 g).

2,5-Diethyl-3,4-dihydro-2H-pyran-2-carbaldehyde has the following NMR spectrum:

$^1$H NMR (CDCl$_3$, 500 MHz): 0.91 ppm (t, 3H, J=7.56 Hz), 0.95 ppm (t, 3H, J=7.46 Hz), 1.58-1.75 ppm (m, 3H), 1.81-1.93 ppm (m, 4H), 2.06-2.12 ppm (m, 1H), 6.38 ppm (s, 1H), 9.55 ppm (s, 1H).

1,4-Diethyl-6,8-dioxa-bicyclo[3.2.1]octane has the following NMR spectrum:

$^1$H NMR (CDCl$_3$, 500 MHz): 0.85-1.03 ppm (m, 6H), 1.04-1.75 ppm (m, 8H), 1.85-2.11 ppm (m, 1H), 3.38-3.43 ppm (m, 1H), 3.80 ppm (d, ~0.53H, J=6.76 Hz), 3.87 ppm (d, ~0.47H, J=6.77 Hz), 5.29 ppm (s, 1H), 5.34 ppm (s, 1H).

Example IV

Preparation of 1,4-Dipropyl-6,8-dioxa-bicyclo[3.2.1]octane (Formula III)

1,4-Dipropyl-6,8-dioxa-bicyclo[3.2.1]octane was prepared according to the same schemes of Examples I and II. The resulting compound has the following NMR spectrum:

$^1$H NMR (CDCl$_3$, 500 MHz): 0.86-0.95 ppm (m, 6H), 1.08-1.51 ppm (m, 8H), 1.54-1.78 ppm (m, 4H+~0.44H), 1.90-1.98 ppm (m, ~0.56H), 3.38-3.42 ppm (m, 1H), 3.79 ppm (dd, ~0.44H, J=6.75, 1.54 Hz), 3.86 ppm (dd, ~0.56H, J=6.76, 1.49 Hz), 5.26 ppm (s, ~0.44H), 5.31 ppm (s, ~0.56H).

Example V

Preparation of 1,4-Diisopropyl-6,8-dioxa-bicyclo[3.2.1]octane (Formula IV)

1,4-Diisopropyl-6,8-dioxa-bicyclo[3.2.1]octane was prepared according to the same schemes of Examples I and II. The resulting compound has the following NMR spectrum:

$^1$H NMR (CDCl$_3$, 500 MHz): 0.85-0.98 ppm (m, 12H), 1.15-1.28 ppm (m, 1H), 1.37-1.50 ppm (m, 2H), 1.58-1.80 ppm (m, 3H), 1.85-1.93 ppm (septet, 1H, J=6.94 Hz), 3.39-3.44 ppm (m, 1H), 3.80 ppm (d, ~0.65H, J=6.76 Hz), 3.87 (d, ~0.35H, J=6.74 Hz), 5.48 ppm (s, ~0.65H), 5.51 ppm (s, ~0.35H).

Example VI

Preparation of 1,4-Dibutyl-6,8-dioxa-bicyclo[3.2.1]octane (Formula V)

1,4-Dibutyl-6,8-dioxa-bicyclo[3.2.1]octane was prepared according to the same schemes of Examples I and II. The resulting compound has the following NMR spectrum:

$^1$H NMR (CDCl$_3$, 500 MHz): 0.85-0.96 ppm (s, 6H), 1.10-1.50 ppm (m, 11H), 1.50-1.81 ppm (m, 5H), 1.91-2.02 ppm (m, 1H), 3.40 ppm (s, 1H), 3.80-3.90 ppm (m, 1H), 5.26-5.34 ppm (m, 1H).

Example VII

Preparation of 1,4-Bis-(1,2-dimethyl-propyl)-6,8-dioxa-bicyclo[3.2.1]octane 1,4-Bis-(1,2-dimethyl-propyl)-6,8-dioxa-bicyclo[3.2.1]octane was prepared according to the same schemes of Examples I and II. The resulting compound has the following NMR spectrum:

$^1$H NMR (CDCl$_3$, 500 MHz): 0.67-1.03 ppm (m, 18H), 1.33-1.52 (m, 2H), 1.54-1.95 ppm (m, 7H), 3.42-3.48 ppm (m, 1H), 3.74-3.97 ppm (m, 1H), 5.44-5.56 ppm (m, 1H).

Example VIII

The odor properties of the above compounds (i.e., Examples II-VII) were evaluated using the intensity scale of 0 to 3, where 0=none, 1=weak, 2=moderate, and 3=strong:

| Index | Compound | Chemical Name | Odor Profile | Odor Intensity |
|---|---|---|---|---|
| 1 | | 1,4-dipentyl-6,8-dioxabicyclo[3.2.1]octane | Metallic, mushroom, and earthy | 3 |
| 2 | | 1,4-diethyl-6,8-dioxabicyclo[3.2.1]octane (Formula II) | Fruity, spicy, herbal, tea-note, anisic, and estragol | 3 |
| 3 | | 1,4-dipropyl-6,8-dioxabicyclo [3.2.1] octane (Formula III) | Latex, fruity, and sour | 3 |

-continued

| Index | Compound | Chemical Name | Odor Profile | Odor Intensity |
|---|---|---|---|---|
| 4 | | 1,4-diisopropyl-6,8-dioxabicyclo[3.2.1]octane (Formula IV) | Fruity, lactonic, green, woody, floral, and waxy | 3 |
| 5 | | 1,4-dibutyl-6,8-dioxabicyclo[3.2.1]octane (Formula V) | Fruity, green, and woody | 2 |
| 6 | | 1,4-bis-(1,2-dimethylpropyl)-6,8-dioxabicyclo[3.2.1]octane | Dirty, chemical, and burnt | 3 |

Compounds 2-5 (i.e., Formulas II-V) were demonstrated to possess an unexpected fruity note, which was lost when the carbon chains contained more than 4 carbons (Compounds 1 and 6).

Example XII

The fragrance formulas exemplified as follows demonstrate that the cyclic acetal compound imparts a fruity note to the formula.

| Ingredients | Parts* + | Parts* − |
|---|---|---|
| Ald C-10 + BHA | 0.20 | 0.20 |
| Ald c-9 "PFG" | 0.10 | 0.10 |
| Allyl Amyl Glycolate Toco "PFG" | 0.20 | 0.20 |
| Abmrettolide | 1.00 | 1.00 |
| Ambroxan Dist | 0.10 | 0.10 |
| Calone 10% DPG | 1.50 | 1.50 |
| Cashmeran | 0.20 | 0.20 |
| Citronellol Coeur | 1.00 | 1.00 |
| Cyclacet | 5.00 | 5.00 |
| Diola BHT | 1.00 | 1.00 |
| Dipropylene Glycol | 7.90 | 9.90 |
| Eth Aceto Acet | 0.30 | 0.30 |
| Floriffol (ELINCS) | 3.00 | 3.00 |
| 1,4-diethyl-6,8-dioxa-bicyclo[3.2.1]octane (Formula II) | 2.00 | — |
| Galaxolide Super | 3.00 | 3.00 |
| Galbaniff BHT (ELINCS) 10% DPG | 0.20 | 0.20 |
| Hedione BHT | 10.00 | 10.00 |
| Heliotropine (Piperonal) (USDEA) | 0.50 | 0.50 |
| Hexenyl Sal, Cis-3 | 0.50 | 0.50 |
| Hexyl Sal | 1.00 | 1.00 |
| Hydroxycit Extra | 2.00 | 2.00 |

-continued

| Ingredients | Parts* + | Parts* − |
|---|---|---|
| Indole 10% DPG | 0.40 | 0.40 |
| Iso E Super BHT | 5.00 | 5.00 |
| Jasmal | 1.00 | 1.00 |
| Kharismal | 10.00 | 10.00 |
| Lilial | 10.00 | 10.00 |
| Linalool Syn | 1.00 | 1.00 |
| Lyral BHT | 20.00 | 20.00 |
| Mandarin Oil HP "PFG" | 0.50 | 0.50 |
| Orange Oil FLA CP "PFG" | 3.00 | 3.00 |
| Rosalva | 2.00 | 2.00 |
| Undecavertol MVB | 0.30 | 0.30 |
| Verdox | 5.00 | 5.00 |
| Zenolide | 1.00 | 1.00 |
| Zestoril 1% DEP | 0.10 | 0.10 |
| Total | 100.00 | 100.00 |

*"+" represents a 1,4-diethyl-6,8-dioxa-bicyclo[3.2.1]octane containing formula; and "−" represents a 1,4-diethyl-6,8-dioxa-bicyclo[3.2.1]octane non-containing formula.

What is claimed is:

1. A compound of formula:

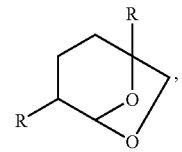

wherein each R represents an identical saturated $C_2$-$C_4$ alkyl straight chain or branched.

2. The compound of claim 1, wherein the compound is 1,4-diethyl-6,8-dioxa-bicyclo[3.2.1]octane.

3. The compound of claim 1, wherein the compound is 1,4-dipropyl-6,8-dioxa-bicyclo[3.2.1]octane.

4. The compound of claim 1, wherein the compound is 1,4-diisopropyl-6,8-dioxa-bicyclo[3.2.1]octane.

5. A method of improving, enhancing, or modifying a fragrance formulation through the addition of an olfactory acceptable amount of a compound of formula:

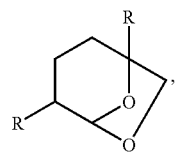

wherein each R represents an identical saturated $C_2$-$C_4$ alkyl straight chain or branched.

6. The method of claim 5, wherein the compound is 1,4-diethyl-6,8-dioxa-bicyclo[3.2.1]octane.

7. The method of claim 5, wherein the compound is 1,4-dipropyl-6,8-dioxa-bicyclo[3.2.1]octane.

8. The method of claim 5, wherein the compound is 1,4-diisopropyl-6,8-dioxa-bicyclo[3.2.1]octane.

9. The method of claim 5, wherein the fragrance formulation is incorporated into a product selected from the group consisting of a perfume, a cologne, a toilet water, a cosmetic product, a personal care product, a fabric care product, a cleaning product, and an air freshener.

10. The method of claim 9, wherein the cleaning product is selected from the group consisting of a detergent, a dishwashing composition, a scrubbing compound, and a window cleaner.

11. The method of claim 5, wherein the olfactory acceptable amount is from about 0.005 to about 10 weight percent of the fragrance formulation.

12. The method of claim 5, wherein the olfactory acceptable amount is from about 0.5 to about 8 weight percent of the fragrance formulation.

13. The method of claim 5, wherein the olfactory acceptable amount is from about 1 to about 7 weight percent of the fragrance formulation.

14. A fragrance formulation containing an olfactory acceptable amount of a compound of formula:

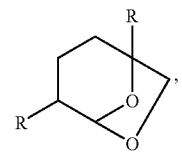

wherein each R represents an identical saturated $C_2$-$C_4$ alkyl straight chain or branched.

15. The fragrance formulation of claim 14, wherein in the compound is 1,4-diethyl-6,8-dioxa-bicyclo[3.2.1]octane.

16. A fragrance product containing an olfactory acceptable amount of the compound of claim 1.

17. The fragrance product of claim 16, wherein in the compound is 1,4-diethyl-6,8-dioxa-bicyclo[3.2.1]octane.

* * * * *